United States Patent [19]

Nixon

[11] Patent Number: 6,130,048
[45] Date of Patent: *Oct. 10, 2000

[54] METHOD OF DIAGNOSING ALZHEIMER'S DISEASE

[75] Inventor: Ralph A. Nixon, Arlington, Mass.

[73] Assignee: McLean Hospital Corporation, Belmont, Mass.

[ * ] Notice: This patent issued on a continued prosecution application filed under 37 CFR 1.53(d), and is subject to the twenty year patent term provisions of 35 U.S.C. 154(a)(2).

[21] Appl. No.: 08/966,756

[22] Filed: Nov. 10, 1997

Related U.S. Application Data

[63] Continuation of application No. 08/282,060, Jul. 28, 1994, Pat. No. 5,686,269.

[51] Int. Cl.$^7$ .................................................... G01N 33/53
[52] U.S. Cl. ............................ 435/7.1; 435/7.92; 436/63; 436/811
[58] Field of Search ................................ 435/4, 7.1, 7.92, 435/7.93, 7.94, 7.95; 436/518, 527, 529, 530, 531, 63, 811

[56] References Cited

U.S. PATENT DOCUMENTS 5,387,742 2/1995 Cordell ........................................ 800/2

OTHER PUBLICATIONS

Hultberg et al., "Diagnostic value of determinations of lysosomal in CSF of patients with neurological disease," *Acta neurologica Scandinavia* 57:201–215 (1978).

Li et al., "Abnormal distribution in cathepsin proteases and endogenous inhibitors (cystatins) in the hippocampus of patients with Alzheimer's disease, parkinsonism–dementia complex on Guam, and senile dementia and in the aged," *Pathological Anatomy and Histopathology* 423:185–194 (1993).

Aoyagi et al., "Enzymatic Changes in Cerebrospinal Fluid of Patients with Alzheimer–Type Dementia," J. Clin. Biochem Nutr., 14:133–139, (1993).

Appleyard et al., "Cholinesterase Activities in Cerebrospinal Fluid of Patients with Senile Dementia of Alzheimer Type," Brain 110:1309–1322 (1987).

Bernstein et al., "Lysosomal Proteinases as Putative Diagnostic Tools in Human Neuropathology: Alzheimer Disease (AD) and Schizophrenia," Acta Histochemica Suppl. Band ILII, S. 1924 (1992).

Burke et al., "Pathology of Epinephrine Neurons in Alzheimer," (Abstract) Soc. Neurosci Abstr 18:557 (1992).

Burke et al., "Increased Cathespin d Immunoreactivity in Inferior Olivary Neurons in Alzheimer's Disease," (abstract) Neurobiol Aging (Abstract No. 233) 15(S1:s57 (1994).

Cataldo et al., "Abnormal Lysosomal Hydrolase mRNA Expression in Neurons from Alzheimer Disease Brain," (Abstract) Soc. Neurosci. Abstr (Abstract No. 510.18) 20:1254 (1994).

Cataldo et al., "Abnormal Localization of Lysosomal Hydrolases in Diffuse Plaques of Alzheimer and Down Syndrome Brains," (Abstract) Neurobiol Aging (Abstract No. 472) 15(S1):S115 (1994).

Cataldo et al., "Enzymatically Active Lysosomal Protease are Associated with Amyloid Deposits in Alzheimer Brain," Proc. Natl. Acad. Sci USA 87:3861–3865 (1990).

Cataldo et al., "Increased Detection of Lysosmal Proteinase Antigens Associated with the Neuropathology of Alzheimer's Disease," Aging and Dementia: Plaques, Tangler, Amyloid 916.5 (Abstract).

Cataldo et al., "Lysosomal Abnormalities in Degenerating Neurons Link Neuronal Compromise to Senile Plaque Development in Alzheimer Disease," Brain Research 640:68–80 (1994).

Cataldo et al., "Lysosomal Proteinase Antigens are Prominently Localized within Senile Plaques of Alzheimer's Disease: Evidence for a Neuronal Origin," Brain Research 513:181–192 (1990).

Cataldo et al., Lysosomal Hydrolases of Different Classes are Abnormally Distributed in Brains of Patients with Alzheimer Disease, Proc. Natl. Acad. Sci. USA 88:10998–11002 (1991).

Cataldo et al., "Lysosomal Abnormalties are markers of Progressive Neuronal Dysfunction in Alzheimer Brain," (Abstract) Soc. Neurosci Abstr. (Abstract No. 81.14) 19:194 (1993).

Cataldo et al., "Lysosomal Hydrolases Colocalize with β–Amyloid in Diffuse Plaques in Alzheimer Brain," (Abstract) Soc. Neurosci. Abstr. (Abstract No. 81.14) 19:194 (1993).

Cuzner et al., "Proteolytic Enzyme Activity of Blood Leukocytes and Cerebrospinal Fluid in Multiple Sclerosis," Ann. Neurol. 4:337–344 (1979).

Diedrich et al., "Neuropathological Changes in Scrapie and Alzheimer's Disease are Associated with Increased Expression of Apolipoprotein E and Cathepsin D in Astrocytes," J. Virology 65:4759–4768 (1991).

Golde et al., "Processing of the Amyloid Protein Precursor to Potentially Amloidongenic Derivatives," Science 225:729–730 (1991).

Hass et al., "Beta–Amyloid Peptide Land a 3kDa Fragment are Derived by Distant Cellular Mechanisms," J. Biol. Chem. 268:3021–3024 (1993).

Kirschke and Barrett, "Lysosomes: Their Role in Protein Breakdown," Academic Press 193–238 (1987).

(List continued on next page.)

*Primary Examiner*—Patricia A. Duffy
*Attorney, Agent, or Firm*—Clark & Elbing LLP; Kristina Bieker-Brady

[57] ABSTRACT

Disclosed is a method of diagnosing Alzheimer's disease in a patient by measuring the level of a lysosomal hydrolase or lysosomal protease inhibitor in the patient's cerebrospinal fluid. The invention also features methods of measuring the progression of the disease and screening therapeutic compositions for treating Alzheimer's disease.

5 Claims, 4 Drawing Sheets

OTHER PUBLICATIONS

Kitaguchi et al., "Determination of Amyloid β Protein Precursors Harboring Active Form of Proteinase Inhibitor Domains in Cerebrospinal Fluid of Alzheimer's Disease Patients by Tryspin–Antibody Sandwich Elisa," Biochemical and Biophysical Research Communications 166(3):1453–1459 (1990).

Matus et al., "Age–Related Increase in a Cathepsin D Like Protease That Degrades Brain Microtubule–Associated Proteins," Amer. Chem Soc. 26:8083–8086 (1987).

McKhann et al., "Clinical Diagnosis of Alzheimer's Disease: Report of the NINCDS–ADRA Work Group Under the Auspices of Department of Health and Human Services Task Force on . . . ," Neurology 34:939–944 (1984).

Mirra et al., "The Consortium to Establish a Registry for Alzheimer's Disease (CERAD)," Neurology 41:479–486 (1991).

Nakamura et al., "Abnormal Distribution of Cathepsins in th eBrain of Patients with Alzheimer's Disease," Neuroscience Letters 130:195–198 (1991).

Nakamura et al., Lysosome Instability in Aged Rat Brain, Neuroscience Letters 97:215–220 (1989).

Nixon et al., "Degradationof Neurofilament Proteins by Purified Human Brain Cathepsin D," J. Neurochemistry 43:507–516 (1984).

Nixon et al. "The Lysosomal System in Neuronal Cell death: A Review," Acad Sci 679:87–109 (1993).

Nixon et al., "The Lysosomal System in Neurons," Annals of the New York Academy of Sciences 674:65–68 (1992).

Nixon et al., "Endosomal–Lysosomal System Abnormalities: An Early Marker of Neuronal Dysfunction in Alzheimer Disease," Neurobiol. Aging 15:(S1):S32 (Abstract No. 133) (1994).

Nixon et al., "Endosomal–Lysosomal System Abnormalities in Alzheimer's Disease: Relationship to Neuronal Dysfunction and Amyloidosis," XIIth Int. Congress Neuropathology (Abstract) (1994).

Nixon et al., "Endosomal–Lysosomal System Abnormalaties: Relationship to Neuronal Dysfunction and Amyloidosis in Alzheimer's Disease," Trans. Am. Soc. Neurochem. (Abstract No. 120) 25:157 (1994).

Nixon et al., "Free Radicals, Proteolysis and the Degeneration of Neurons in Alzheimer Disease: How is the β–Amyloid Link?," Neurobiol. Aging 15:463–469 (1994).

Nixon et al., "Increased Neuronal Cathepsin D Gene Expression and Active Release of Competent Protease in Alzheimer Disease," (Abstract No. 612.2) Soc. Neurosci. Abstr. 20:1484 (1994).

Nixon et al., "Lysosomal Proteolysis in Alzheimer Brain: Possible Roles in Neuronal Cell Death and Amyloid Formation," Elsevier Press 133–46 (1991).

Omar et al., "Acid Phosphatase Activity in Senile Plaques and Cerebralspinal Fluid of Patients with Alzheimer's Disease," Atch Pathol Lab Med 117:166–169 (1993).

Palmert et al., "Antisera to an Amino–Terminal Peptide Detect the Amyloid Protein Precursor of Alzheimer's Disease and Recognize Senile Plaques," Academic Press, Inc. 156(1):432–437 (1988).

Perry et al., "Amyloid Precursor Protein in Senile Plaques of Alzheimer Disease," The Lancet Sep. 24, 1988.

Riekkinen et al., "Proteinase in Human Cerebrospinal Fluid," J. Neurological Sciences, 7:97–106 (1968).

Ryan et al., "Pro–IL–1B Processed to its Mature Form by the Cysteine Proteinase Cathepsin B: A Potential Therapeutic Target in Alzheimer Disease," Soc. for Neurosci. Abstracts 18:97–2 (1992).

Schwagerl et al., "Elevated Levels of Cathepsin D in Cerebrospinal Fluid from Alzheimer Disease Patients," $4^{th}$ Intl. Conf on Alz Dis and Related Dis. McLean Hospital, Harvard Univ. (1994).

Selkoe et al., "β–Amyloid precursor protein of Alzheimer disease occurs as 110–to 135–kilodalton membrane–associated proteins in neural and nonneural tissues," Proc. Natl. Acad. Sci. 85:7341–7345 (1988).

Shoji et al., "Production of the Alzheimer amyloid β Protein by Normal Proteolytic Processing," Science 258:126–130 (1992).

Schwagerl et al., Neurobiology of Aging, 15 Supplement 1, S115, received in Library on Jul. 7, 1994.

Takeda et al., "Change of Cathespin D Activities in Vinglastine–Injected Rabbit Brain and Alzheimer's Disease Brain," Neurochemical Research 11L:117–119 (1986).

Takeuchi et al., "Immunoassay and Activity of Calcium–Activated Neutral Proteinase (mCANP):Distribution in Soluble and Membrane–Associated Fractions in Human and . . . ," Neurochemistry 58:1526–1532 (1992).

Villanova et al., "Rimmed Vacuoles of Inclusion Body Myositis and Oculopharyngeal Muscular Dystrophty Contain Amyloid Precursor Protein and Lysosomal Markers," Brain Research 603:343–347 (1993).

Wester et al., "Ventricular Cerebrospinal Fluid Monamine Transmitter and Metabilite Concentrations Reflect Human Brain Neurochemistry in Autopsy cases," J. Neurochemistry 54:1148–1156 (1990).

Whitaker et al., "Immunicytochemical Localization of Cathepsin D in Rat Neural Tissue," Brain Research 216:109–124 (1981).

Wirak et al., "Deposits of Amyloid β Protein in the Central Nervous System of Transgenic Mice," Science 253:323–325 (1991).

Wolozin et al., "A Neuronal Antigen in the Brains of Alzeheimer Patients," Science 232:648–650 (1986).

Woessner et al., "Purification and Properties of Cathepsin D from Bovine Uterus," J. Biol. Chem., 246(7):1051–1060, (1971).

Wur et al. eds., "Handbook of Experimental Immunology," vol. 1: Immunochemistry published 1986 pp. 27.1–27.20.

Sigma Chemical Company Catalogue, 1992, p. 218.

DAKO Corporation Catalogue and Price List, 1993, p. 16.

Matsubara etal , J. Clin Exp. Med, 145:907–908, 1988.

Matsubara etal, Ann. Neurol, 28:561–567, 1990.

Matsubara etal, Prog.Clin. Biol. Res., 317:707 Abstract 1989.

Hinds etal, Neurobiology of Aging, 15(1):21–27, 1994.

Ii etal, Virchuous Archiv A Pathol Anat , 423:185–194, 1993.

Brugge etal, Ann. Neurol, 32:193–197, 1992.

Bernstein et al, Brain Research Bulletin, 33(5):477–481, 1994.

Matsubara etal, in Alzheimer's Disease and Related Disorders, 1989 Alan R. Liss Inc, p707–714.

deLustig et al, Reviews in the Neurosciences, 5:213–225 (1994).

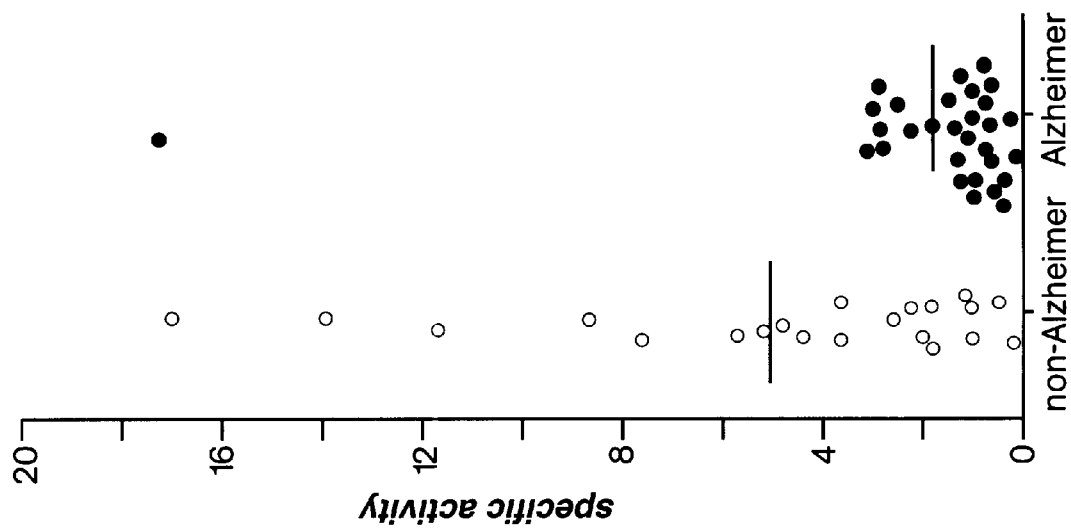
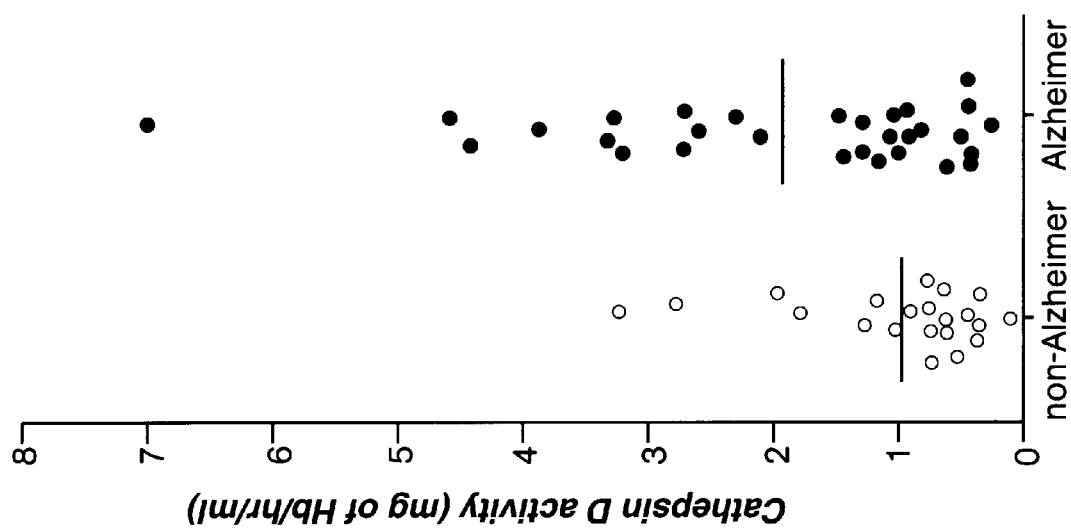
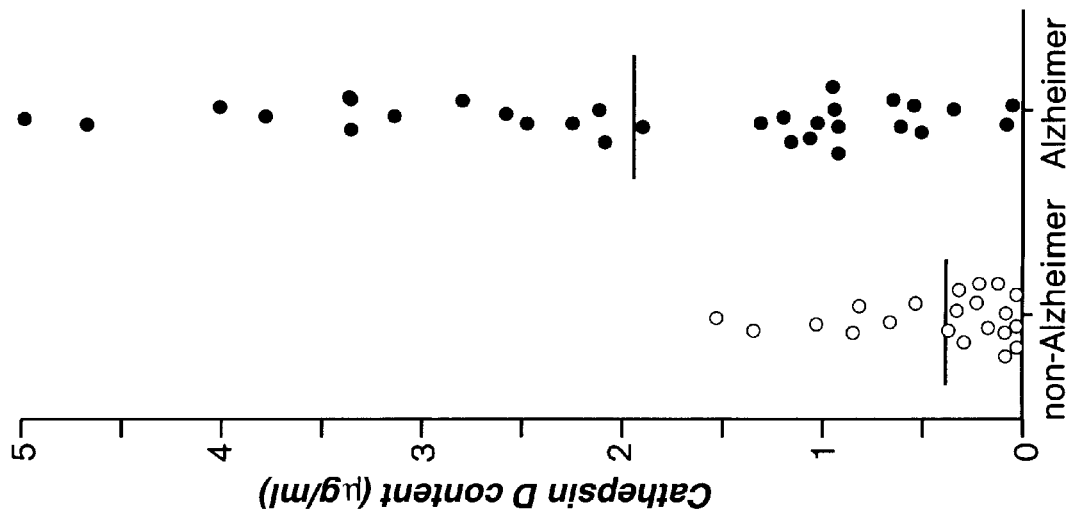

METHOD OF DIAGNOSING ALZHEIMER'S DISEASE

This is a continuation of application Ser. No. 08/282,060, filed Jul. 28, 1994, now U.S. Pat. No. 5,686,269.

BACKGROUND OF THE INVENTION

This invention relates to diagnosing Alzheimer's disease.

Alzheimer's disease (AD) is a progressive neurodegenerative disorder which is characterized by memory loss, impairment in abstract thinking, impaired judgment, personality change, and insidious onset of the disease in the absence of other specific causes of dementia. Eventually, the AD patient becomes completely incapacitated, and death results from debilitation or infection.

Under the guidelines established by the National Institute of Neurological and Communicative Disorders and Stroke, and the Alzheimer's Disease and Related Disorders Association (NINCDS/ADRDA), a clinical diagnosis of probable AD involves the administration of a series of neuropsychologic tests (see Table 1). Many of the signs of AD occur as part of the normal process of aging or may result from other forms of dementia, and thus the present NINCDS/ADRDA standards require the absence of an alternative explanation for the symptoms.

Table 1: NINCDS/ADRDA Criteria for Clinical Diagnosis of Alzheimer's Disease

Criteria for the clinical diagnosis of probable Alzheimer's disease include

Dementia established by clinical examination and documented by the Mini-Mental State Examination, Blessed Dementia Scale, or some similar examination and confirmed by neuropsychologic tests Deficits in two or more area of cognition Progressive worsening of memory and other cognitive functions No disturbance of consciousness Onset between ages 40 and 90, most often after age 65

Absence of systemic disorders or other brain diseases that could account for the progressive deficits in memory and cognition The diagnosis of probable Alzheimer's disease is supported by Progressive deterioration of specific cognitive functions such as language (aphasia), motor skills (apraxia), and perception (agnosia)

Impaired activities of daily living and altered patterns of behavior

Family history of similar disorders, particularly if confirmed neuropathologically Laboratory results as follows: normal puncture as evaluated by standard techniques; normal pattern or nonspecific changes in EEG, such as increased slow-wave activity; and evidence of cerebral atrophy of CT with progression documented by serial observation Other clinical features consistent with the diagnosis of probable Alzheimer's disease, after exclusion of causes of dementia other than Alzheimer's disease, include Plateaus in the course of progression of the illness Associated system of depression, insomnia, incontinence, delusions, illusions, hallucinations, sexual disorders, weight loss, and catastrophic verbal, emotional, or physical outbursts Other neurologic abnormalities in some patients, especially with more advance disease and including motor signs such as increased muscle tone, myoclonus, or gait disorder Seizures in advanced disease CT normal for age Features that make the diagnosis of probable Alzheimer's disease uncertain or unlikely include Sudden, apoplectic onset Focal neurologic finds such as hemiparesis, sensory loss, visual field deficits, and incoordination early in the course of the illness Seizures or gait disturbances at the onset or very early in the course of the illness Clinical diagnosis of possible Alzheimer's disease May be made on the basis of the dementia syndrome, in the absence of other neurologic, psychiatric, or systemic disorders sufficient to cause dementia and in the presence of variations in the onset, presentation, or clinical course May be made in the presence of a second systemic or brain disorder sufficient to produce dementia, which is not considered to be the cause of the dementia Should be used in research studies when a single, gradually progressive, severe cognitive deficit is identified in the absence of another identifiable cause Criteria for diagnosis of definite Alzheimer's disease are The clinical criteria for probable Alzheimer's disease Histopathologic evidence obtained from a biopsy or autopsy Classification of Alzheimer's disease for research purposes should specify features that may differentiate subtype of the disorder, such as Familial occurrence Onset before age 65

Presence of trisomy 21

Coexistence of other relevant conditions, such as Parkinson's disease

Note: NINCDS=National Institute of Neurological and Communicative Disorders and Stroke; ADRDA= Alzheimer's Disease and Related Disorders Association Under the current standards established by the Consortium to Establish a Registry for Alzheimer's Disease (CERAD), a post-mortem diagnosis of definite AD involves a series of histopathologic test on biological samples obtained from the patient. Tables 2 and 3 indicate that the CERAD neuropathologic diagnosis is derived from an evaluation of senile plague frequency and a clinical history of dementia.

TABLE 2

| Age of patient at death (yrs) | Age-related plaque scores* | | | |
|---|---|---|---|---|
| | Frequency of plaques[+] | | | |
| | None | Sparse | Moderate | Frequent |
| <50 | O | C | C | C |
| 50–75 | O | B | C | C |
| >75 | O | A | B | C |

*An age-related plaque score is determined using patient's age along with plaque frequency in the most heavily affected neocortical section.
[+]Based on section of frontal, temporal, or parietal cortex with maximum involvement.
For purpose of this protocol, the letter circled corresponds to the following assessment:
O = NO histologic evidence of Alzheimer's disease.
A = Histologic findings are UNCERTAIN evidence of Alzheimer's disease.

TABLE 2-continued

Age-related plaque scores*

| Age of patient at death (yrs) | Frequency of plaques+ | | | |
| --- | --- | --- | --- | --- |
| | None | Sparse | Moderate | Frequent |

B = Histologic findings SUGGEST the diagnosis of Alzheimer's disease.
C = Histologic findings INDICATE the diagnosis of Alzheimer's disease.

TABLE 3

Neuropathology diagnosis: Diagnostic criteria for Alzheimer's disease

| | |
| --- | --- |
| Normal (with respect to AD or other dementing processes (choose one) | a. No histologic evidence of Alzheimer's disease (0 score), and no clinical history of dementia, and absence of other neuropathologic lesions likely to cause dementia<br>b. An "A" age-related plaque score and no clinical history of dementia<br>c. A history of dementia and absence of any neuropathologic lesions likely to cause dementia |
| Definite | "C" age-related plaque score, and clinical history of dementia, and presence or absence of other neuropathologic lesions likely to cause dementia |
| CERAD NP probable* | "B" age-related plaque score, and clinical history of dementia, and presence or absence of other neuropathologic disorders likely to cause dementia |
| CERAD NP possible* (choose one) | a. "A" age-related plaque score, and clinical history of dementia, and presence or absence of other neuropathologic lesions that could cause dementia<br>b. "B" or "C" age-related plaque score and absence of clinical manifestations of dementia |

*Not to be confused with the NINCDS-ADRDA clinical criteria (McKhann et al., Neurology 1984; 34:939–944).
The age-related plaque score is integrated with the presence or absence of a clinical history of dementia to arrive at a diagnostic level of certainty with regard to Alzheimer's disease.

SUMMARY OF THE INVENTION

I have, for the first time, detected the lysosomal hydrolase cathepsin D (CD) in human cerebrospinal fluid (CSF), and I have discovered that the CSF of AD patients contains elevated levels of CD relative to non-AD patients.

Accordingly, the invention features a method of diagnosing AD in a patient, involving determining the level of a lysosomal hydrolase in the patient's CSF and comparing the level of the lysosomal hydrolase to normal levels. Thus, lysosomal hydrolases provide biochemical markers for the diagnosis of AD; an increase in the level of a lysosomal hydrolase, relative to the normal level, is indicative of AD. The invention provides a rapid and convenient method of distinguishing AD from other dementias.

In a related aspect, the invention features a method of diagnosing AD in a patient by measuring the level of a lysosomal protease inhibitor in the CSF of a patient. An increase in the level of the inhibitor, relative to the normal level of the inhibitor, is indicative of AD.

In another aspect, the invention features a method of following the rate of AD progression, involving assaying the CSF for changes in the level of a lysosomal hydrolase over the course of time. An increase in the level of the lysosomal hydrolase signifies that the state of disease has advanced; a decrease in the lysosomal hydrolase level indicates amelioration of the disease.

In a related aspect, the rate of AD progression is monitored by assaying the CSF of the patient for changes in the levels of an inhibitor of a lysosomal protease inhibitor. An increase in the level of the lysosomal protease inhibitor indicates that the disease state has advanced, while a decrease in the inhibitor level signifies amelioration of the disease.

The invention further features a method of determining whether a candidate therapeutic composition is useful for treating AD. The level a lysosomal hydrolase in the CSF of a patient diagnosed with AD is measured prior to, and following, administration of the candidate therapeutic composition. A decrease in the level of lysosomal hydrolase indicates that the composition is useful for treating AD.

In a related aspect, the invention features a method of determining whether a candidate therapeutic composition is useful for treating AD, involving measuring the level of a lysosomal protease inhibitor in the CSF of the patient prior to, and following, administration of the candidate therapeutic composition.

Preferred lysosomal hydrolases include cathepsin D, cathepsin G, cathepsin L, cathepsin H, hexosaminidase A, and hexosaminidase B. Preferred lysosomal protease inhibitors include cystatin C and stefin A.

CSF useful in the invention includes ventricular and lumbar CSF. Thus, the invention can be used for clinical and postmortem diagnoses of AD.

In preferred embodiments, the level of the lysosomal hydrolase or lysosomal protease inhibitor is measured in an immunoassay (e.g., Western blot, ELISA, inhibition ELISA, immunoprecipitation, slot or dot blot assays, immunostaining, RIA, and fluorescent immunoassays). Antibodies which are immunoreactive with a chosen lysosomal hydrolase or lysosomal protease inhibitor are appropriate for use in such assays. For example, antibodies which are raised by immunization of a mammal with antigenic determinants of the chosen lysosomal hydrolase or lysosomal protease inhibitor are useful in immunoassays. Antibodies for detecting each of the lysosomal hydrolases and lysosomal protease inhibitors useful in the invention are currently available and known in the art (e.g., for anti-CD antibodies, see Nixon and Marotta, 1984, J. Neurochem. 43:507–516). Also useful in the invention are combinations of antibodies to detect a CSF lysosomal hydrolase or lysosomal protease inhibitor. Such combinations of antibodies can be used, for example, to enhance the detection of a lysosomal hydrolase or lysosomal protease inhibitor, or to detect more than one lysosomal hydrolase or lysosomal protease inhibitor in the CSF sample. Thus, a diagnosis of AD can be made on the basis of the detection of more than one lysosomal hydrolase and/or lysosomal protease inhibitor in the CSF of the patient.

In other embodiments, non-immunologic techniques, such as SDS-PAGE and activity assays in polyacrylamide gels can be used to measure the level of the lysosomal hydrolase or lysosomal protease inhibitor. Generally, the level of lysosomal hydrolase or lysosomal protease inhibitor is measured in the CSF of a patient suspected of having AD, and compared with the level found in non-AD patients. An elevated level of the lysosomal hydrolase or lysosomal protease inhibitor is indicative of AD. The absolute levels of the lysosomal hydrolases and lysosomal protease inhibitors are expected to differ from protein to protein, and the extent to which each protein is elevated in the CSF of AD patients (relative to normal patients) also will vary from protein to protein. Generally, a CSF lysosomal hydrolase or lysosomal protease concentration which is at least 1.5 times, or more preferably 2 times, or most preferably 3 times the concentration in normal patients is indicative of AD. For examples, a CD concentration which is two times the normal level of CD indicates AD in the tested patient. Generally, a ventricular CSF CD level of at least 1.7 μg/ml, more preferably 2.0 μg/ml, indicates AD.

The level of lysosomal hydrolase can also be determined by measuring its enzymatic activity. For example, CD cleaves proteins preferentially between two large hydrophobic amino acid residues; thus, the level of CD in a sample can be determined by assaying for protein fragments produced by the proteolytic cleavage of substrates such as hemoglobin (Hb) (Kirschke and Barrett, *Lysosomes: Their Role in Protein Breakdown,* 193–238, Academic Press, 1987). In one preferred embodiment, the ability of the lysosomal hydrolase to cleave a protein substrate is measured in the presence and absence of an inhibitor of its activity. For example, the level of CD can be measured as pepstatin-inhibitable hydrolysis of hemoglobin at the optimal pH of 3.2. The combination of a specific inhibitor of aspartyl proteinases (pepstatin) and the acid pH optimum pH 3.2 distinguishes the hydrolysis of hemoglobin by CD from hydrolysis by other enzymes. Generally, a CD activity level of at least 1.5 times, or more preferably 2 times, the activity level in non-AD patients is indicative of AD.

Prior to measuring the level of the lysosomal hydrolase or lysosomal protease inhibitor by any method, the protein concentration of the CSF can be increased by any of the well known protein concentration techniques (e.g., ammonium sulfate precipitation; see, e.g., Ausbel et al., *Current Protocols in Molecular Biology*, John Wiley & Sons, 1989). The chosen lysosomal hydrolase or lysosomal protease inhibitor in the CSF sample can be partially purified by standard protein purification methods (e.g., ion exchange chromatography, affinity chromatography, high performance liquid chromatography, and immunoprecipitation; see, e.g., Ausubel et al., supra).

By "cerebrospinal fluid" is meant the fluid which surrounds the bulk of the nervous system, as described in *Physiological Basis of Medical Practice* (ed. J. B. West, Williams and Wilkins, Baltimore, Md., 1985). Cerebrospinal fluid, as used herein, includes ventricular and lumbar CSF.

By "lysosomal hydrolase" is meant any of the acid hydrolases which are normally present intracellulary in the endosomes, lysosomes, related endosomal-lysosomal compartments, and residual bodies of cells, including neurons and other neural cells. Lysosomal hydrolases include, without limitation, lysosomal proteases such as cathepsins B, G, H, and L; non-protease lysosomal hydrolases such as hexosaminidases A and B; and other proteins of various enzyme classes.

By "lysosomal protease inhibitor" is meant a compound which prevents or inhibits the activity of a lysosomal protease. Examples of lysosomal protease inhibitors are cystatin C and stefin A.

By "normal levels" of a lysosomal hydrolase or lysosomal protease inhibitor is meant the normal range of amounts of the lysosomal hydrolase or lysosomal protease inhibitor present in healthy individuals who do not suffer from AD or any other disease in which the level in CSF is affected.

By "immunoassay" is meant any method of detecting proteins which involves the use of antibodies (e.g., Western blot, ELISA, inhibition ELISA, immunoprecipitation, slot or dot blot assays, immunostaining, RIA, and fluorescent immunoassay).

By "activity" of a lysosomal protease is meant the ability of the protease to hydrolyze peptide bonds (e.g., CD cleaves the internal peptide bonds of proteins, usually between two hydrophobic residues).

By "activity" of a non-protease lysosomal hydrolase is meant the ability of the enzyme to cleave a substrate (e.g., an oligosaccharide) with the addition of $H_2O$ at the point of cleavage.

By "activity" of a lysosomal protease inhibitor is meant the ability of the compound to prevent or inhibit cleavage by a lysosomal protease as defined above.

Other features and advantages of the invention will be apparent from the following description of the preferred embodiments thereof, and from the claims.

DETAILED DESCRIPTION

The drawings will first be briefly described.

FIG. 2a is a schematic representation of CD content in AD and non-AD patients.

FIG. 2b is a schematic representation of CD activity in AD and non-AD patients.

FIG. 2c is a schematic representation of CD specific activity in AD and non-AD patients.

The following examples are meant to illustrate, but no limit, the methods of the present invention. Other suitable modifications and adaptations of the conditions normally encountered in immunodiagnostics which are obvious to those skilled in the art are within the scope of the invention.

COLLECTION OF CSF

Techniques for collecting CSF are well known in the art (see, e.g., Appleyard et al., 1987, Brain 110: 1309; and Wester et al., 1990, J. Neurochem. 54: 1148). In the present example, CSF was collected from the lateral ventricle of the brain using at 16-gauge spinal needle within 24 hours of death. Cellular debris in the sample was removed by centrifugation at 15,0000×g. In several cases, the pelleted material was analyzed for CD, and the level of CD in the pellet was less than 1% of the CD in the CSF sample. Lumbar CSF can be isolated using a similar technique (see, e.g., The Merck Manual, 1746–1748, 12th edition D. N. Holvey, ed., Merck, Sharp, and Dohne Research Publishing, N.J., 1972).

ELEVATED CD CONCENTRATIONS IN AD PATIENTS

A 20 ml sample of ventricular CSF was collected after death from 30 AD patients, 14 patients with Huntington disease (HD), and 7 patients with other neurodegenerative diseases (including 2 with diffuse Lewy body disease, 3 with Pick's disease, 1 with non-Alzheimer neurofibrillary degeneration, and 1 with multiple sclerosis). All of the Alzheimer's patients met the neuropathologic criteria for definite AD developed by the Consortium to Establish a Registry for Alzheimer's Disease (see Mirra et al., 1991, Neurology, 41: 479–486). HD is accompanied by a gradual loss of the mental faculties ending in dementia, and thus HD patients and patients suffering from other neurological disorders are a useful control group for identifying biochemical markers which can distinguish AD from other dementias. These late-onset dementias are sometimes difficult to distinguish clinically from AD.

Figure 1A:
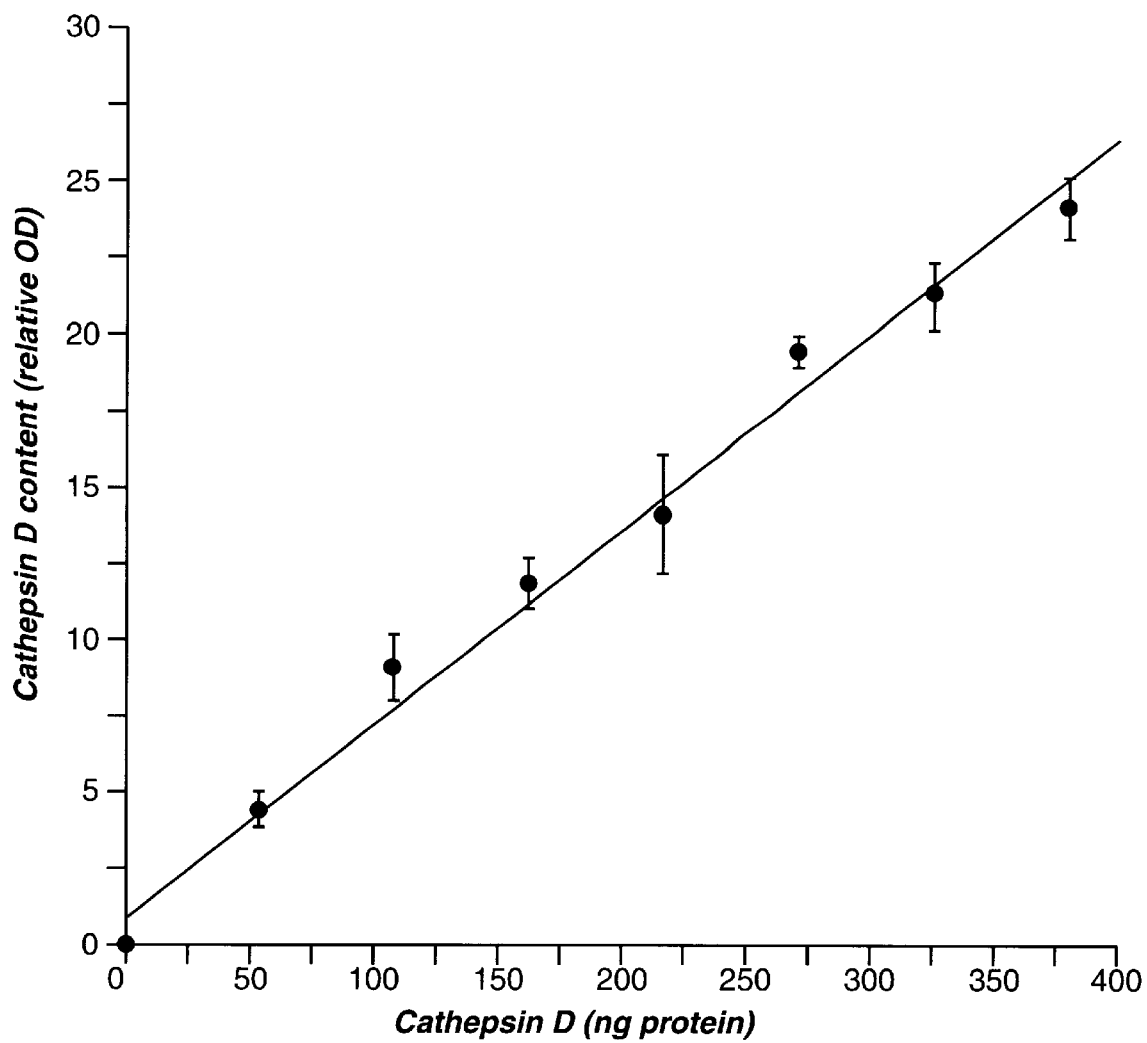
FIG. 1a is a graph showing that CD immunoreactivity on immunoblots of CSF is linearly related to the weight of purified human brain CD.

The concentration of CD in 100 μl samples of CSF was determined by Western blot immunoassay using a 1:5,000 dilution of polyclonal sheep antiserum directed against human brain CD (Nixon and Marotta, 1984, J. Neurochem. 43: 507–516). In addition, anti-CD monoclonal antibodies (Oncogene Science, Cambridge, Mass.) and polyclonal antisera (DAKO, Carpinteria, Calif.; Cortex Biochem, San Leandro, Calif.; and Athens Research, Athens, Ga.) were used in the Western blot immunoassays to confirm the identity of CD. Purified human brain CD was used as a protein standard (see Nixon and Marotta, supra and Takekuchi et al., 1992, J. Neurochem. 58: 1526–1532). In these Western blot immunoassays, immunoreactivity of the mature 32-kD polypeptide chain of CD was linearly related to the weight of purified human brain CD within the range of 50 and 400 ng (see FIG. 1a).

As shown in Table 4, the level of immunoreactive CD (1.98 μg/ml CSF) was more than four times higher in the AD patients than in patients suffering from other late-onset neurological diseases (0.44 μg/ml CSF). In 90% of the AD patients, the level of CD exceeded the mean value for CD in the neurologic disease controls, and all of the control subjects had CD levels which were lower than the mean level for the AD subjects. The results of these studies are independent of post-mortem variables and patient age. The data presented in Table 4 also indicate that the CD level expressed as ng/mg total protein was elevated almost 4-fold in AD patients. Generally, a CD level of at least 1.7 ng/mg total CSF protein is indicative of AD. Thus, these data indicate that the level of CD immunoreactive protein can also serve as a clinical marker of AD.

TABLE 4

Cathepsin D Levels in Cerebrospinal Fluid in Alzheimer's Disease and Other Neurologic Diseases

| Item | Alzheimer | Total Non-Alzheimer[a] | Huntington | Other |
|---|---|---|---|---|
| Number | 30 | 21 | 14 | 7 |
| Postmortem Interval | 14 (1–28) | 13.4 (4–26) | 14.3 (4–26) | 11 (5–20) |
| Age | 77 (50–97) | 57 (24–80) | 53 (24–71) | 69 (60–80) |
| Males/Females | 24/6 | 14/7 | 7/7 | 7/0 |
| Total protein (mg/ml) | 1.48 ± 0.21[b] | 1.01 ± 0.16 | 0.70 ± 0.18[+] | 1.63 ± 0.19 |
| CD content (μg/ml CSF) | 1.98 ± 0.31 | 0.44 ± 0.09 | 0.32 ± 0.10* | 0.69 ± 0.18[+] |
| CD activity (mg Hb/hr/ml CSF) | 1.92 ± 0.29 | 1.01 ± 0.17[+] | 0.76 ± 0.10[±] | 1.59 ± 0.42 |
| Specific activity (mg Hb/hr/μg CD) | 1.81 ± 0.56 | 4.98 ± 0.99[¶] | 6.15 ± 1.38* | 2.64 ± 0.58 |
| CD content (μg/mg protein) | 1.94 ± 0.33 | 0.49 ± 0.11* | 0.54 ± 0.17[±] | 0.39 ± 0.08[+] |
| CD activity (μg Hb/hr/mg CSF protein) | 1.91 ± 0.30 | 1.51 ± 0.25 | 1.80 ± 0.34 | 0.92 ± 0.18 |

Legend to TABLE 4

TABLE 4-continued

Cathepsin D Levels in Cerebrospinal Fluid in Alzheimer's Disease and Other Neurologic Diseases

| Item | Alzheimer | Total Non-Alzheimer[a] | Huntington | Other |
|---|---|---|---|---|

[a]Data for the combined groups of patients with Huntington disease and those with other neurologic diseases (designated "other" in this Table).
[b]Values in all analyses are means ±S.E.M. for the indicated number of cases.
[+]$p < 0.05$ student's "t" test vs. Alzheimer mean
[±]$p < 0.01$
*$p < 0.001$
[¶]$p < 0.005$
[#]$p < 0.0005$

ELEVATED CD ACTIVITY LEVELS IN AD PATIENTS

Figure 1B:
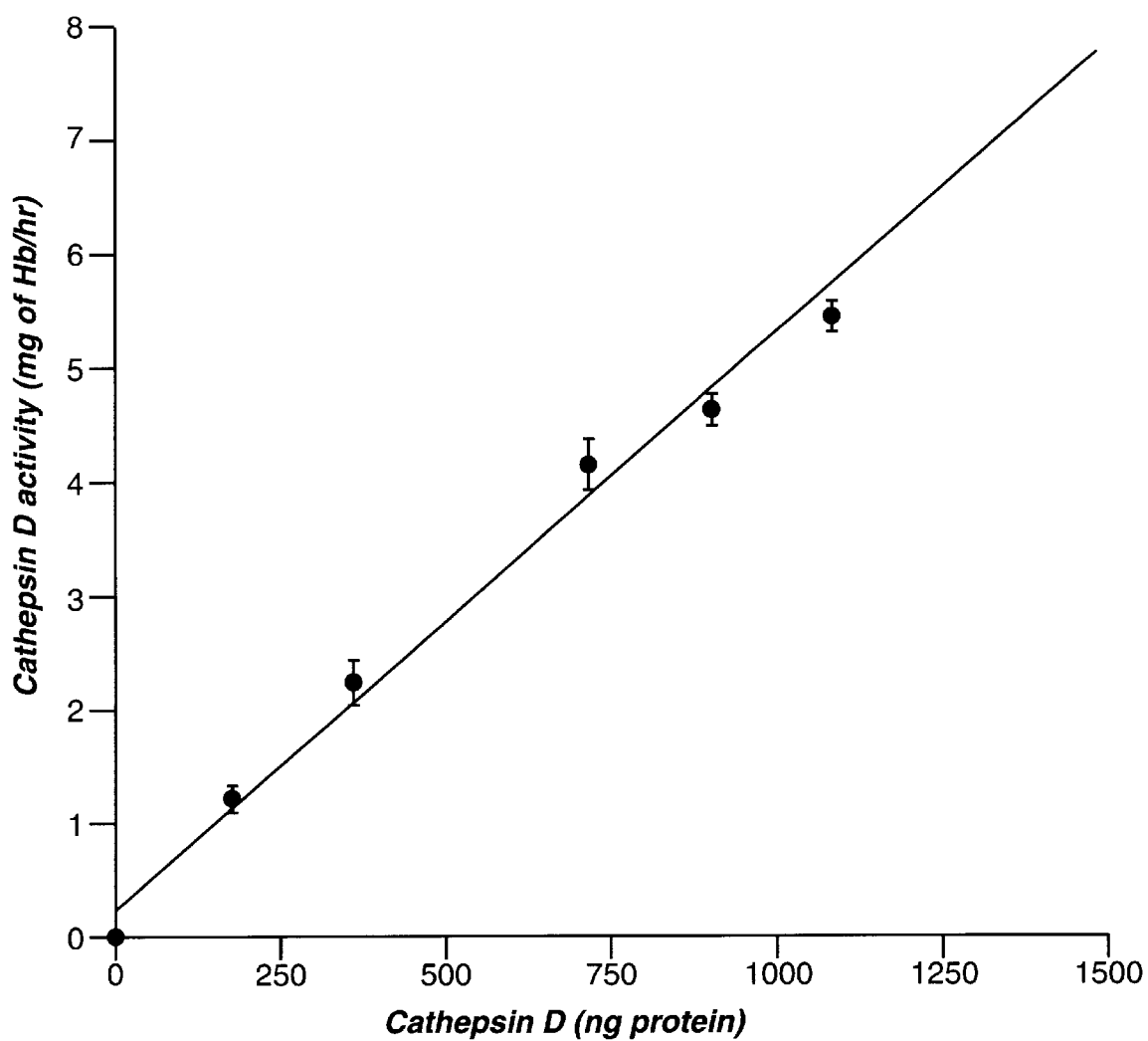
FIG. 1b is a graph showing that CD activity in CSF is linearly related to the weight of purified human brain CD.

CD activity levels in the CSF of 30 AD, 14 HD patients, and 7 patients afflicted with other neurodegenerative diseases were measured after death as pepstatin-inhibitable hydrolysis of [$^{14}$C]-hemoglobin (Hb) at ph3.2. CD activity was linearly related to the weight of purified human brain CD within the range of 18 and 150 ng (FIG. 1b). In AD patients, the activity of CD was elevated approximately two-fold relative to the CD activity in HD patients. As shown in Table 4, the CD activity level in Alzheimer's CSF was 1.92 mg Hb/hr/ml CSF, and in non-Alzheimer's CSF, the level was 1.01 mg Hb/hr/ml. The observation that CD activity levels are higher in AD patients than in patients afflicted with other neurologic disorders supports the use of CD activity level as an indicator of AD. Regression analysis indicated that CD activity in CSF was unrelated to post-mortem interval ($r=0.026$ and $0.044$, respectively) and age ($r=0.239$ and $0.018$, respectively). The data presented in Table 4 also indicate that the CD specific activity is lower in AD patients than in non-AD patients (1.81 mg Hb/hr/ml in Alzheimer's CSF and 4.98 mg Hb/hr/ml in non-Alzheimer's CSF), suggesting that the abnormally accumulated CD of AD patients includes both enzymatically active and inactive forms.

The CSF of AD patients contains elevated levels of CD relative to patients who do not suffer from AD. Thus, the invention provides a method for using biochemical markers to diagnose AD, monitor the rate of AD progression, and screen for AD therapeutic compositions.

In diagnosing AD, the CSF of the patient is collected, and the level of CD is compared with normal CD levels, Generally, a CSF CD level of at least 1.7 μg/ml is indicative of AD. A variety of protein detection methods (e.g., immunoassays, SDS-PAGE, and activity assays) can be used to assay for CD, and an elevated CD level indicates probable AD. A diagnosis of AD may involve an assay of CD levels in conjunction with the detection of any of the AD symptoms outlined in Tables 1, 2, and 3. By measuring the change in CD levels as a function of time, the progression of AD can be monitored; lumbar CSF is particularly useful for this purpose. An increase in CD levels over time signifies that the state of the disease has advanced; a decrease in CD levels is indicative of amelioration of the disease. In addition, the invention facilitates the screening of therapeutic compositions, with a decrease in the CD level signifying that a composition is useful for treating AD.

OTHER EMBODIMENTS

Other embodiments are within the following claims. For example, if desired, CD or the other lysosomal hydrolases and lysosomal protease inhibitors can be partially purified from the CSF sample. Partial purification of the protein facilitates detection of the protein in CSF samples having low levels of immunoreactive or enzymatically active forms of the protein. Any of the methods commonly available to those skilled in the art (e.g., ion exchange chromatography, affinity chromatography, and immunoprecipitation) may be used for partial purification.

Figure 3:
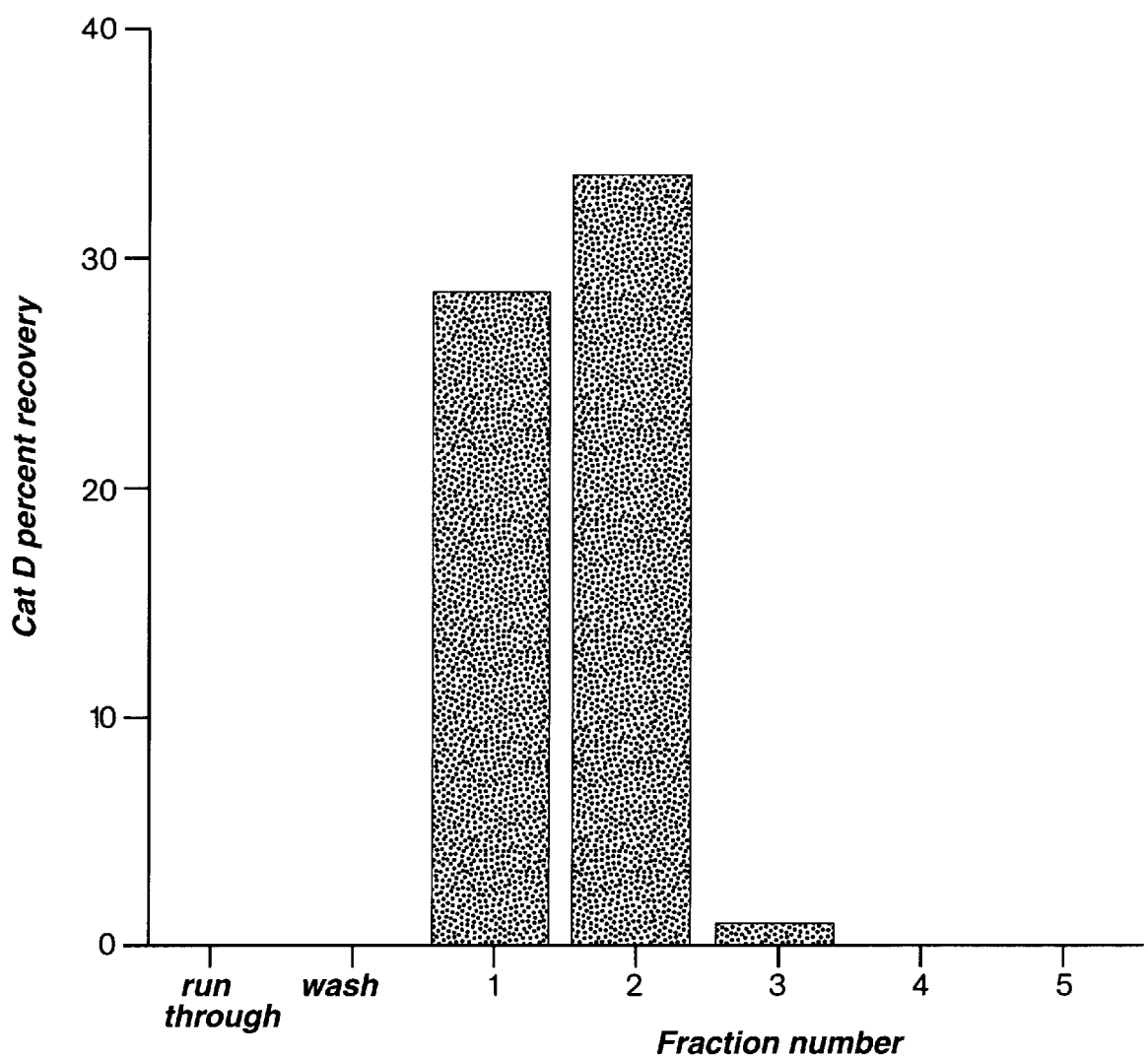
FIG. 3 is a histogram of the elution profile of ventricular CSF CD from a pepstatin column.

For example, CD has been partially purified from a 1–5 ml CSF sample as follows. The CSF sample was adjusted to 0.2 M NaCl and pH 4.5 with 0.1 volume of 1 M acetate buffer (pH 4.5). This fraction was mixed for 2 hours with 0.5 g of diaminodipropylamine-pepstatinyl-Sepharose 6 B (Pierce Chemicals; Rockport, Ill.) equilibrated with 0.1 M acetate buffer (pH 4.5) containing 0.2 M NaCl. The mixture then was poured into a 5×0.25 cm column, and, after washing the column with the same buffer (10 ml/1hour), the enzyme was eluted with 0.1 M Tris-HCl (pH 8.6) containing 0.2 M NaCl. FIG. 3 is a histogram which shows that all of the CD activity in CSF binds to the column and is eluted in the first two 1 ml fractions by the pH 8.6 buffer. In this case, the recovery of the enzyme from the column is at least 90% of the activity measured in the sample prior to chromatography. In addition, recovery of the immunoreactive CD also is greater than 90%.

Also within the invention is the use of proteins other than CD to diagnose and monitor the progression of AD. The brains of AD patients accumulate a variety of lysosomal hydrolases and lysosomal protease inhibitors extracellularly within senile plaques (Cataldo et al., 1991, PNAS 88:10998–11002). Such lysosomal hydrolases and lysosomal protease inhibitors include cathepsins D, B, G, L, and H; hexosaminidases A and B; cystatin C; and stefin A. I have determined, for the first time, that the lysosomal hydrolase CD is present in CSF. This observation suggests that the CD which accumulates extracellularly in AD brains in cleared via the CSF. Accordingly, the other lysosomal proteins which accumulate extracellularly in AD brains should be present in CSF as well. Indeed, I have detected several of these enzymes, including cathepsins B and H, cystatin C, and hexosaminidase A in CSF obtained from AD patients. Partial protein purification using standard methods will facilitate detection of other lysosomal proteins as well. Using the guidance provided herein, the protein levels which are indicative of AD can be readily determined by one skilled in the art.

Also within the invention is the use of lumbar CSF in the diagnosis and monitoring of AD. As is the case for detection of the diagnostic proteins in ventricular CSF, protein purification methods may be used to facilitate detection of the lysosomal hydrolases and lysosomal protease inhibitors in lumbar CSF. Indeed, I have detected CD in 100 µL samples of lumbar CSF; as expected, CD levels are lower in lumbar CSF than in ventricular CSF. Western blot immunoassays indicate that the concentration of CD in AD patients is approximately 0.1 µg/ml lumbar CSF, and this level of CD is elevated relative to the CD level found in lumbar CSF of non-AD patients. In addition, I have detected CD activity in lumbar CSF of non-AD patients; in these patients, the CD activity level is approximately 0.05 mg Hb/hr/mg total protein. Using the guidance provided herein, one skilled in the art can readily determine the lumbar CSF protein levels which are indicative of AD.

What is claimed is:

1. A method for diagnosing probable Alzheimer's disease in a patient, said method comprising determining the level of cystatin C in cerebrospinal fluid of said patient, and comparing said level of cystatin C to normal levels, wherein an increase in cystatin C levels relative to normal indicates said diagnosis of probable Alzheimer's disease in said patient.

2. The method of claim 1, wherein said cerebrospinal fluid is ventricular cerebrospinal fluid.

3. The method of claim 1, wherein said cerebrospinal fluid is lumbar cerebrospinal fluid.

4. A method of measuring Alzheimer's disease progression in a patient, comprising determining the level of cystatin C in cerebrospinal fluid of said patient at a first time point, and determining the level of said cystatin C in cerebrospinal fluid at a second time point, wherein an increase in said cystatin C at said second time point signifies that the state of Alzheimer's disease has progressed.

5. The method of claim 4, wherein said cerebrospinal fluid is lumbar cerebrospinal fluid.

* * * * *

UNITED STATES PATENT AND TRADEMARK OFFICE
CERTIFICATE OF CORRECTION

PATENT NO. : 6,130,048
DATED : October 10, 2000
INVENTOR(S) : Ralph A. Nixon

It is certified that error appears in the above-identified patent and that said Letters Patent is hereby corrected as shown below:

Title page,
Item [56], References Cited, U.S PATENT DOCUMENTS, insert
-- 4,968,603   11/6/90   Slamon et al.   435/6 --; and
-- 4,935,341   6/19/90   Barbmann et al.   435/6 --;

FOREIGN PATENT DOCUMENTS, and therein insert
-- WO9322339 --; -- WO9322424 --; -- WO8906692 --; -- WO9014357 --; -- WO9115230 --; -- WO9118921 --; and -- WO9212174 --;

OTHER PUBLICATIONS,
-- Benveniste, E.N. et al., P.N.A.S., "Purification and characterization of a human T-lymphocyte-derived glial growth promoting factor," 82:3930-3934, June 1985. --;
-- Kimura, H. et al., "Nature, Structure, expression and function of a Schwannoma derived growth factor," 348:257-260, November 15, 1990. --;
-- Falls et al., Cell, ARIA, A Protein that stimulates acetypcholine receptor synthesis, is a member of the Neu Ligand family, 72:801-815 (1993) --;
-- Plowman et al., Nature, Heregulin induces tyrosine phosphorylation of HER4/ $p180^{erbB4}$, 366: 473. --;
-- Brookes et al., "Purification and Preliminary Characterization of a Glial Growth Factor from the Bovine Pituitary", J. Biol. Chem. 255: 18, 8374-8377 (September 1980). --;
-- Brookes et al., "The neuron as a source of mitogen: its influence on the proliferation of glial and non-neural cells", Garrod and Feldman eds, pp. 309-327 (1980). --;
-- Lemke et al. "An immunochemical Approach to the Purification and Characterization of Glial Growth Factor", Monoclonal Antibodies to Neural Antigens, McKay, Raff and Reichardt, eds. pp. 133-140 (1981). --;

UNITED STATES PATENT AND TRADEMARK OFFICE
CERTIFICATE OF CORRECTION

PATENT NO. : 6,130,048
DATED : October 10, 2000
INVENTOR(S) : Ralph A. Nixon

It is certified that error appears in the above-identified patent and that said Letters Patent is hereby corrected as shown below:

Column 1,
Line 67, "myocionus" should be -- myoclonus --;

Column 5,
Line 7, "examples," should be -- example, --; and

Column 6,
Line 37, "no" should be -- not --.

Signed and Sealed this

Seventh Day of May, 2002

Attest:

Attesting Officer

JAMES E. ROGAN
Director of the United States Patent and Trademark Office